(12) United States Patent
He et al.

(10) Patent No.: US 8,553,975 B2
(45) Date of Patent: Oct. 8, 2013

(54) METHOD AND APPARATUS FOR WIDE-BAND IMAGING BASED ON NARROW-BAND IMAGE DATA

(75) Inventors: Zhihua He, Reading, MA (US); Nathaniel McCaffrey, Portola Valley, CA (US); Jason Sproul, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 388 days.

(21) Appl. No.: 12/873,643

(22) Filed: Sep. 1, 2010

(65) Prior Publication Data

US 2011/0069315 A1 Mar. 24, 2011

Related U.S. Application Data

(60) Provisional application No. 61/244,323, filed on Sep. 21, 2009.

(51) Int. Cl.
*G06K 9/60* (2006.01)

(52) U.S. Cl.
USPC .......................................................... 382/162

(58) Field of Classification Search
USPC .................................. 382/162; 348/222.1
See application file for complete search history.

(56) References Cited

U.S. PATENT DOCUMENTS

| | | | |
|---|---|---|---|
| 5,078,150 A | 1/1992 | Hara et al. | |
| 5,827,190 A | 10/1998 | Palcic et al. | |
| 5,889,554 A * | 3/1999 | Mutze | 348/273 |
| 6,364,829 B1 * | 4/2002 | Fulghum | 600/160 |
| 6,366,694 B1 * | 4/2002 | Acharya | 382/167 |
| 6,730,019 B2 | 5/2004 | Irion | |
| 2003/0158470 A1 | 8/2003 | Wolters et al. | |
| 2005/0054937 A1 | 3/2005 | Takaoka et al. | |
| 2006/0104505 A1 * | 5/2006 | Chen et al. | 382/162 |
| 2006/0155166 A1 | 7/2006 | Takahashi et al. | |
| 2006/0197923 A1 | 9/2006 | Edlinger et al. | |
| 2007/0041720 A1 | 2/2007 | Iketani | |
| 2007/0058050 A1 * | 3/2007 | Innocent | 348/222.1 |

(Continued)

FOREIGN PATENT DOCUMENTS

EP  2 106 736 A2  10/2009

OTHER PUBLICATIONS

Graham D. Finlayson et al., "The Maximum Ignorance Assumption with Positivity," Final Program and Proceedings of the IS&T/SID, Fourth Color Imaging Conference: Color Science, Systems and Applications, pp. 202-205.

(Continued)

*Primary Examiner* — Kara E Geisel
(74) *Attorney, Agent, or Firm* — Bookoff McAndrews, PLLC

(57) ABSTRACT

In one embodiment, an imaging method may include receiving an intensity value of a first spectral channel associated with a pixel location. The intensity value of the first spectral channel may be based on electromagnetic radiation reflected from an object after being emitted from a narrow-band electromagnetic radiation source. The method may further include defining an intensity value of a second spectral channel based on the intensity value of the first spectral channel. The second spectral channel may be associated with a spectral region of electromagnetic radiation different from a spectral region of electromagnetic radiation associated with the first spectral channel. The method may also include associating the intensity value of the second spectral channel with the pixel location.

20 Claims, 7 Drawing Sheets

(56) References Cited

U.S. PATENT DOCUMENTS

2007/0078299 A1 4/2007 Ayame et al.
2007/0100207 A1 5/2007 Ueno et al.
2009/0065679 A1 3/2009 Tanimoto

OTHER PUBLICATIONS

Kobus Barnard et al., "A Data Set for Color Research," Color Research and Application, vol. 27. No. 3, pp. 147-151, Jun. 2002.
Kazuhiro Gono, "An Introduction to High Resolution Endoscopy and Narrowband Imaging," Comprehensive Atlas of High Resolution Endoscopy and Narrowband Imaging, Wiley-Blackwell, Chapter 2, pp. 9-22, (Jun. 11, 2007).
Sina Farsiu et al., "Multi-Frame Demosaicing and Super-Resolution of Color Images," IEEE Transactions on Image Processing, IEEE Service Center, Piscataway, NJ, vol. 15, No. 1, pp. 1-39, (Jan. 1, 2006).
International Search Report and Written Opinion mailed on Dec. 20, 2010, in corresponding International Application PCT/US2010/049224 (12 pages).

\* cited by examiner

METHOD AND APPARATUS FOR WIDE-BAND IMAGING BASED ON NARROW-BAND IMAGE DATA

CROSS REFERENCE TO RELATED APPLICATION

This patent application claims the benefit of priority under 35 U.S.C. §§119 and 120 to U.S. Provisional Patent Application No. 61/244,323, filed Sep. 21, 2009, which is herein incorporated by reference in its entirety.

FIELD OF THE DISCLOSURE

Embodiments of the invention relate generally to narrow-band imaging, and, in particular, to methods and apparatus for defining wide-band image data based on narrow-band image data.

BACKGROUND OF THE DISCLOSURE

An image detector can be configured to receive and convert light reflected from an object, after being emitted from a light source, into one or more color channel signals. The color channel signal(s) can be used to define image data that can then be used to produce one or more images of the object on a display. For example, a full-color image of the object can be produced when the object is illuminated by a white light source. Many consumer products, such as video cameras and digital cameras, have imaging systems with this capability.

If a narrow-band light source is used to illuminate an object, a narrowband image can be produced. This can be referred to as narrow-band imaging. A narrow-band light source is a light source associated with a narrow spectrum of electromagnetic radiation compared to a spectrum of electromagnetic radiation associated with a wide-band light source. Imaging using a wide-band light source can be referred to as wide-band imaging. In some applications, a narrow-band light source can be used to illuminate an object so that a narrow-band image that enhances specific features of the object can be produced. For example, a red color light source can be used with an endoscopic system to help medical practitioners readily identify certain tissue structures that are enhanced when illuminated by the red color light.

In some applications, both narrow-band imaging and wide-band imaging are desired. Because known imaging system do not produce images associated with a spectrum of light that is broader than the spectrum of light emitted by the light source, often two different light sources are used in these systems—a narrow-band light source and a wide-band light source. For example, known image processing systems are not capable of producing full-color images when the only light source included in the system is a red color light source. Thus, a need exists for methods and apparatus for defining wide-band image data based on narrow-band image data especially in applications where using a narrow-band light source is desirable.

SUMMARY OF THE DISCLOSURE

One exemplary aspect of the present disclosure is directed to an imaging method. The method may include receiving an intensity value of a first spectral channel associated with a pixel location, wherein the intensity value of the first spectral channel is based on electromagnetic radiation reflected from an object after being emitted from a narrow-band electromagnetic radiation source. The method may also include defining an intensity value of a second spectral channel based on the intensity value of the first spectral channel, wherein the second spectral channel is associated with a spectral region of electromagnetic radiation different from a spectral region of electromagnetic radiation associated with the first spectral channel. The method may further include associating the intensity value of the second spectral channel with the pixel location.

Various embodiments of the disclosure may include one or more of the following aspects: calculating the intensity value of the first spectral channel based on a demosaic algorithm; the spectral region of electromagnetic radiation associated with the first spectral channel may be separate from the spectral region of electromagnetic radiation associated with the second spectral channel; the pixel location may be associated with a pixel, wherein a spectral region of electromagnetic radiation associated with the pixel may be modified in response to associating the intensity value of the second spectral channel with the pixel location; receiving an intensity value of a third spectral channel associated with the pixel location, wherein the third spectral channel may be associated with a spectral region of electromagnetic radiation different from the spectral region of electromagnetic radiation associated with the second spectral channel, wherein defining the intensity value of the second spectral channel may be based on the intensity value of the third spectral channel; defining the intensity value of the second spectral channel may be based on a linear mathematical relationship; defining the intensity value of the second spectral channel may be based on a coefficient associated with the first spectral channel and a coefficient associated with the second spectral channel; defining a first pixel of a first image based on the intensity value of the first spectral channel and the intensity value of the second spectral channel, wherein the first pixel may be associated with the pixel location; and defining a second pixel of a second image based on the intensity value of the first spectral channel and not based on the intensity value of the second spectral channel, wherein the second pixel may be associated with the pixel location.

Another exemplary aspect of the present disclosure is directed to another imaging method. The method may include receiving a plurality of signals based on electromagnetic radiation reflected from an object after being emitted from a first electromagnetic source configured to emit electromagnetic radiation having a first spectral region of electromagnetic radiation. At least a portion of an image of the object may be based on the plurality of signals, the portion of the image being associated with a second spectral region of electromagnetic radiation broader than the first spectral region of electromagnetic radiation.

Various embodiments of the disclosure may include one or more of the following aspects: the second spectral region of electromagnetic radiation may include at least a portion of the first spectral region of electromagnetic radiation; the image may be a red-green-blue (RGB) image, the first spectral region may be a narrow-band spectral region, and the second spectral region may be a red-green-blue (RGB) spectral region; the electromagnetic radiation may be reflected at a first time, and the plurality of signals may be a first plurality of signals; receiving a second plurality of signals based on electromagnetic radiation reflected at a second time from the object after being emitted from a second electromagnetic radiation source having a third spectral region of electromagnetic radiation, wherein the third spectral region of electromagnetic radiation may be different than the first spectral region of electromagnetic radiation; defining the at least a portion of the image of the object may be based on the second plurality of signals; the second spectral region of electromagnetic radiation may include at least a portion of the first spectral region of electromagnetic radiation and at least a portion of the third spectral region of electromagnetic radiation; and defining the at least a portion of the image of the object may be based on a back projection transform matrix.

Yet another exemplary aspect of the present disclosure is directed to a computer-readable medium storing a set of instructions for executing a process. The process may include receiving a signal based on electromagnetic radiation emitted from a narrow-band electromagnetic radiation source, calculating a portion of a first pixel based on the signal, and calculating a portion of a second pixel based on the portion of the first pixel and based on a correlation between narrow-band responsiveness data and wide-band responsiveness data.

Various embodiments of the disclosure may include one or more of the following aspects: the portion of the first pixel may be associated with an intensity level of a first spectral channel, and the portion of the second pixel may be associated with an intensity level of a second spectral channel, wherein the intensity level of the first spectral channel may be different than the intensity level of the second spectral channel; triggering emission of electromagnetic radiation at a specified intensity level from the narrow-band electromagnetic radiation source; and triggering a display of a portion of a first image based on the first pixel during a time period and triggering a display of a portion of a second image based on the second pixel during the time period.

In this respect, before explaining at least one embodiment of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure.

As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

DETAILED DESCRIPTION

Figure 1:
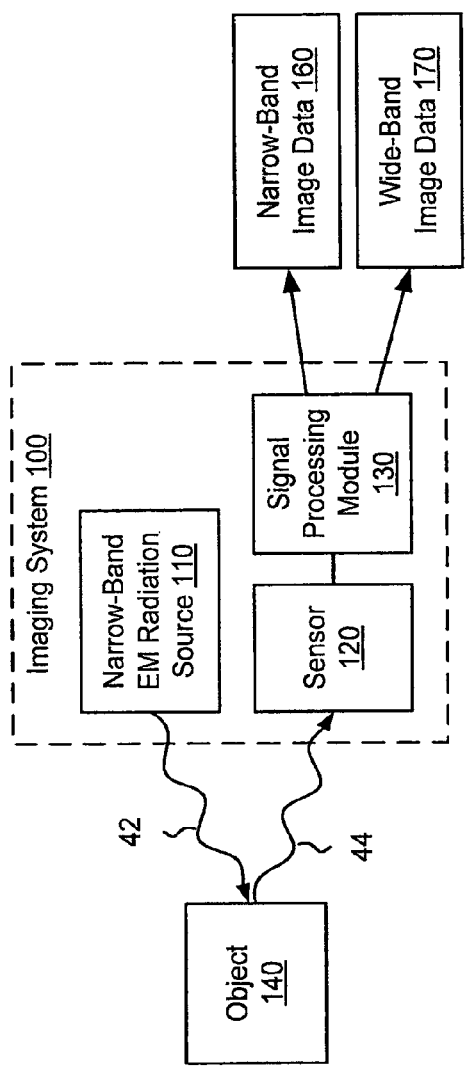
FIG. 1 is a schematic block diagram that illustrates a signal processing module configured to define wide-band image data based on narrow-band image data, according to an embodiment of the invention.

FIG. 1 is a schematic block diagram that illustrates a signal processing module 130 configured to define wide-band image (WBI) data 170 based on narrow-band image (NBI) data 160, according to an embodiment of the invention. The narrow-band image data 160 is defined by the signal processing module 130 based on a signal from a sensor 120 that is configured to receive electromagnetic (EM) radiation emitted 42 from a narrow-band electromagnetic radiation source 110 and reflected 44 (e.g., scattered) from an object 140 (e.g., a target, a target object). The narrow-band electromagnetic radiation source 110 can also be referred to as a narrowband electromagnetic light source. Electromagnetic radiation includes, for example, radio waves, microwaves, terahertz radiation, infrared radiation, visible light, ultraviolet radiation, x-rays, gamma rays, and so forth.

The wide-band image data 170 is associated with a spectral region of electromagnetic radiation that is broader than a spectral region of electromagnetic radiation that is associated with the narrow-band image data 160. In other words, at least a portion of the spectral region of electromagnetic radiation associated with the wide-band image data 170 falls outside of the spectral region of electromagnetic radiation associated with the narrow-band image data 160. In some embodiments, at least a portion of the wide-band image data 170 is associated with wavelengths of electromagnetic radiation that fall outside of the spectral region of electromagnetic radiation associated with the narrow-band image data 160. The portion of the spectral region of electromagnetic radiation that falls outside of the spectral region associated with the narrow-band image data 160 can be calculated based on, for example, a mathematical relationship.

In this embodiment, the signal processing module 130 is a component within an imaging system 100 that also includes the narrow-band electromagnetic radiation source 110 and the sensor 120. The signal processing module 130 can be a hardware-based module (e.g., a digital signal processor (DSP), a field programmable gate array (FPGA)) and/or a software-based module (e.g., a module of computer code, a set of processor-readable instructions that can be executed at a processor). In some embodiments, the signal processing module 130 can include and/or can be associated with a memory (not shown in FIG. 1) and/or a processor (not shown in FIG. 1). The narrow-band electromagnetic radiation source 110 can be any type of electromagnetic radiation source configured to emit electromagnetic radiation. For example, the narrow-band electromagnetic radiation source 110 can be a light emitting diode (LED), a tungsten-based emitter, an infrared source, and so forth.

The sensor 120 can be any type of sensor that can be used to receive electromagnetic radiation, and in response, define a signal such as, for example, an analog signal (e.g., a voltage-based signal, a frequency-based signal) or a digital signal. The sensor 120 can be a collection of individual sensors that can be referred to as a pixel or as pixel sensors. The sensor 120 can include a filter (not shown) configured to separate different spectral regions of electromagnetic radiation that can be associated with a spectral channel and one or more photo-detecting elements (not shown). The photo-detecting elements can be part of, for example, a charge-coupled device (CCD) and/or a complementary metal-oxide-semiconductor (CMOS) device. The filter can be, for example, a Bayer filter, a red-green-blue-cyan (RGBC) filter, a cyan-yellow-magenta-green (CYMG) filter, and/or a dichroic prism filter. In some embodiments, the sensor 120 can be a Foveon X3 sensor, a thermal imaging sensor, a video camera tube, a gamma camera sensor, an x-ray sensor, etc. In some embodiments, the sensor 120 can be used with, for example, a lens or set of lenses (not shown); which may comprise additional filtering elements.

A spectral channel can be associated with a band of wavelengths and can be centered around, for example, a color such as a primary color (e.g., red, blue, green). In some embodiments, when a spectral channel is centered around a wavelength (e.g., a wavelength measured in nm) that corresponds with a substantially uniform color (e.g., a green color), the spectral channel can be referred to as a color channel. Different spectral regions of electromagnetic radiation can be associated with one or more signals that can each be produced by, for example, different CCDs within sensor 120 or multiple sensors (not shown).

The narrow-band image data 160 can be used to define a narrow-band image of the object 140 (not shown in FIG. 1) and the wide-band image data 170 can be used to define a wide-band image of the object 140 (not shown in FIG. 1). Image data can include, for example, any information that can be used to produce an image. The image data can include information such as, for example, a raw signal defined by a portion of the sensor 120 (e.g., an individual pixel sensor), a pixel location value associated with a portion of the sensor 120, a pixel location value associated with a display (not shown in FIG. 1), a saturation value, a luma value, a chroma value, and/or an intensity value (e.g., an intensity value expressed as a digital number (DN), expressed in lumens (1 m) or candela (cd) per square foot ($ft^2$)) associated with a spectral region of electromagnetic radiation (e.g., a spectral channel). The narrow-band image data 160 and/or the wide-band image data 170 can be defined after a demosaic algorithm (e.g., a demosaic color interpolation) and/or a compression algorithm has been executed.

In some embodiments, a narrow-band image and/or a wide-band image can be displayed on one or more displays (not shown in FIG. 1) such as a liquid crystal display (LCD). The image based on the narrow-band image data 160 can be used to define features that may be difficult for a person viewing the image to distinguish in a wide-band image (e.g., tissue structures in an image of a patient's internal organs, blood vessels within a tissue). In some embodiments, one or more images based on the narrow-band image data 160 and/or one or more images based on the wide-band image data 170 can be displayed on one or more displays simultaneously. For example, a narrow-band image and a wide-band image can be overlaid on a single display after pseudo-color post-processing. The simultaneous display of the narrow-band image and the wide-band image can be used by a person viewing the images to distinguish features and/or understand portions that would be difficult to discern without the simultaneous display. In some embodiments, the wide-band image data 160 and/or the narrow-band image data 170 can be used to produce at least a portion of a video.

In some embodiments, the narrow-band image data 160 can be characterized as narrow-band because the spectral region of electromagnetic radiation associated with the narrow-band image data 160 is based on a spectral region of electromagnetic radiation emitted from the narrow-band electromagnetic radiation source 110. In some embodiments, the narrow-band electromagnetic radiation source 110 can be a radiation source that emits a spectral region of electromagnetic radiation that is substantially less than a spectral region of electromagnetic radiation emitted from a white light source. For example, the narrow-band electromagnetic radiation source 110 can be configured to emit a narrow spectral region centered around a specified wavelength such as 530 nanometers (nm) or centered around a specified color such as red (e.g., between 630 nm and 700 nm). In some embodiments, the wide-band image data 160 can be used to produce a full-color image (e.g., red-green-blue (RGB) image) associated with a spectral region of electromagnetic radiation substantially corresponding to a white light source. In some embodiments, the terms narrow-band and wide-band are used to distinguish relative ranges of spectral regions.

Figure 2:
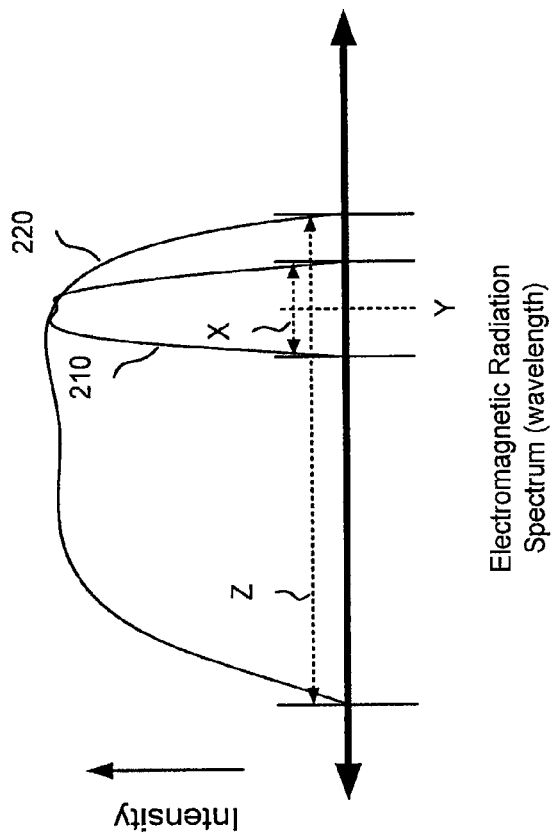
FIG. 2 is a schematic graph of an electromagnetic radiation spectrum that illustrates relative spectral regions of electromagnetic radiation associated with FIG. 1, according to an embodiment of the invention.

FIG. 2 is a schematic graph of an electromagnetic radiation spectrum that illustrates relative spectral regions of electromagnetic radiation associated with FIG. 1, according to an embodiment of the invention. The narrow-band electromagnetic radiation source 110 can be configured to emit electromagnetic radiation 42 (as shown in FIG. 1) with an intensity profile 210 that has a spectral region X centered about wavelength Y as shown in FIG. 2. Accordingly, the electromagnetic radiation reflected 44 from the object 140 and transmitted as a signal from the sensor 120 to the signal processing module 130 (as shown in FIG. 1) will have a spectral region substantially equal to spectral region X as shown in FIG. 2. Furthermore, the narrowband image data 160 will be associated with (e.g., based on) a spectral region of electromagnetic radiation that is substantially equal to spectral region X because the narrow-band image 160 will be defined based on the signal from the sensor 120.

The wide-band image data 170 is associated with (e.g., based on) electromagnetic radiation that has a spectral region Z. As shown in FIG. 2, in some embodiments, the spectral region Z can correspond with a spectral region of electromagnetic radiation from a wide-band electromagnetic source (e.g., wide-band light source) that has an intensity profile 220. In some embodiments, the spectral region X can be centered around a wavelength Y that corresponds with the color red and the spectral region Z can correspond with a spectral region of electromagnetic radiation from a white light source.

Referring back to FIG. 1, the wide-band image data 170 can be defined by the signal processing module 130 based on a correlation between narrow-band responsiveness data and wide-band responsiveness data. The narrow-band responsiveness data can be based on two or more signals defined by the sensor 120 (e.g., an archetypical sensor) in response to electromagnetic radiation emitted from the narrow-band electromagnetic radiation source 110. In other words, the narrow-band responsiveness data can be representative of a responsiveness of the sensor 120 to electromagnetic radiation emitted from the narrow-band electromagnetic radiation source 110. The wide-band responsiveness data can represent a signal defined by sensor 120 (e.g., an archetypical sensor) in response to electromagnetic radiation emitted from a wide-band electromagnetic radiation source (not shown in FIG. 1). In other words, the wide-band responsiveness data can be representative of a responsiveness of the sensor 120 to electromagnetic radiation emitted from the wideband electromagnetic radiation source. More details related to wide-band responsiveness data and narrow-band responsiveness data are discussed in connection with FIG. 5.

In some embodiments, the correlation between the narrow-band responsiveness data and the wide-band responsiveness data can be expressed as a mathematical relationship. The mathematical relationship can be a function of narrow-band image data 160, can be accessed by the signal processing module 130, and can be used to the calculate the wide-band image data 170. More details related to the nature of the correlation (e.g., the mathematical relationship) will be discussed in connection with FIG. 3.

In some embodiments, the imaging system 100 can be used in a medical device such as an endoscope or a tool that has an imaging capability. In some embodiments, the narrow-band electromagnetic radiation source 110 and/or the sensor 120 can be disposed in a separate housing from the signal processing module 130.

Figure 3A:
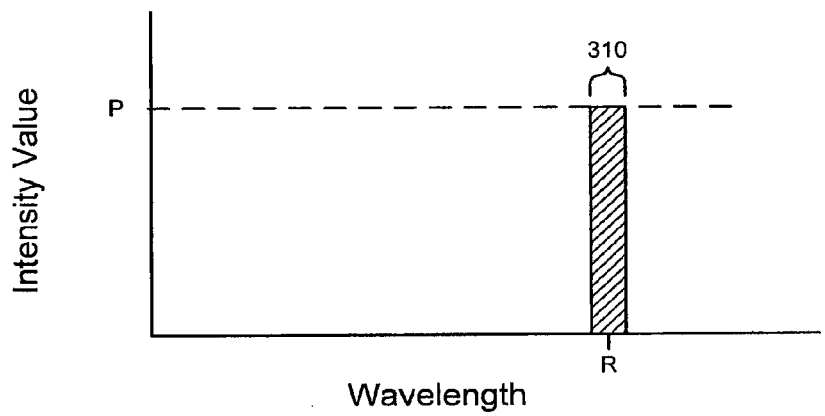
FIG. 3A is a schematic graph that illustrates an electromagnetic radiation emission from a narrow-band electromagnetic radiation source, according to an embodiment of the invention.

FIG. 3A is a schematic graph that illustrates an electromagnetic radiation emission from a narrow-band electromagnetic radiation source, according to an embodiment of the invention. The narrow-band electromagnetic radiation source can be a narrow-band electromagnetic radiation source such as that shown in FIG. 1. The narrow-band electromagnetic radiation source can be configured to emit a spectral region 310 of electromagnetic radiation centered around a wavelength R at an intensity value of P. In this embodiment, the wavelength R corresponds with a red color in a visible electromagnetic spectrum. Because the narrow-band electromagnetic radiation source is configured to emit electromagnetic radiation centered around a wavelength that corresponds with a red color, the narrow-band electromagnetic radiation source can be referred to as a red-color-channel electromagnetic radiation source.

Figure 3B:
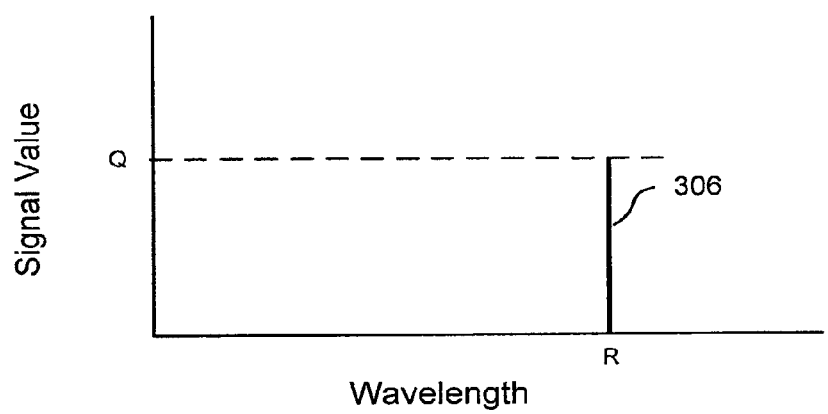
FIG. 3B is a schematic graph that illustrates a response of a pixel sensor to electromagnetic radiation reflected from an object after being emitted from the narrow-band electromagnetic radiation source described in connection with FIG. 3A, according to an embodiment of the invention.

FIG. 3B is a schematic graph that illustrates a response of a pixel sensor to electromagnetic radiation reflected from an object after being emitted from the narrow-band electromagnetic radiation source described in connection with FIG. 3A, according to an embodiment of the invention. The pixel sensor can be a pixel sensor from a sensor such as that shown in FIG. 1 (e.g., sensor 120). As shown in FIG. 3B, the pixel sensor of the electromagnetic radiation sensor produces a signal 306 at a signal value of Q at wavelength R (e.g., at the red wavelength). The signal value can be, for example, an analog value (e.g., a voltage-based signal, a frequency-based signal), or a digital value (e.g., digital number (DN)). In some embodiments, the signal value can be or can be correlated with, for example, an intensity value.

In the embodiment shown in FIG. 3B, the pixel sensor is configured to detect electromagnetic radiation centered around wavelength R and produce the signal 306 in response. In other words, the pixel sensor is configured to respond to (e.g., have a significant response to) electromagnetic radiation associated with color channel R (also can be referred to as spectral channel R). Accordingly, the pixel sensor can be referred to as an R color channel pixel sensor. Because the wavelength R corresponds to a wavelength that has a red color, the pixel sensor can also be referred to as a red-color-channel pixel sensor.

In some embodiments, the electromagnetic radiation sensor can have pixel sensors configured to respond to electromagnetic radiation associated with additional color channels such as a green color channel. The pixel sensors that are not configured to respond to the electromagnetic radiation emitted from the narrow-band electromagnetic radiation source, however, will not be able to produce a signal.

Any parameter values associated with signal 306 (e.g., the signal value) can be associated with a pixel location value. In some embodiments, the pixel location value can be based on an x/y coordinate system or can be a unique alphanumeric value associated with the pixel sensor. For example, the pixel sensor can be an individual sensor from a matrix of pixel sensors such as pixel sensor 444 shown in FIG. 4.

Figure 4:
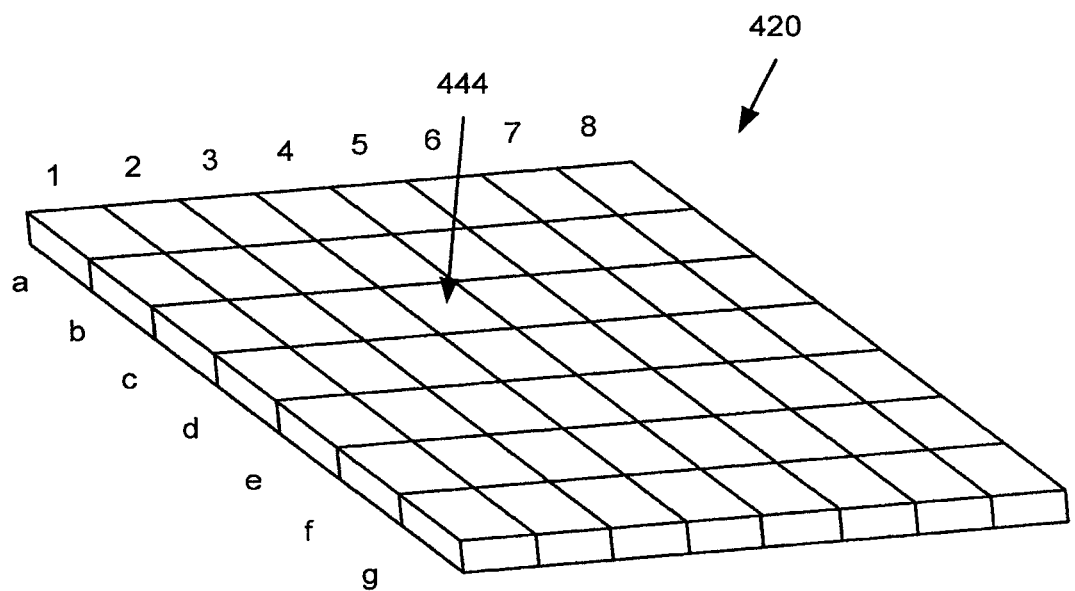
FIG. 4 is a schematic diagram that illustrates a matrix of pixel sensors that collectively can be referred to as an electromagnetic radiation sensor, according to an embodiment of the invention.

FIG. 4 is a schematic diagram that illustrates a matrix of pixel sensors that collectively can be referred to as an electromagnetic radiation sensor 440, according to an embodiment of the invention. As shown in FIG. 4, pixel sensor 444 is associated with pixel location value (c, 4). In some embodiments, the electromagnetic radiation sensor 440 can have one or more pixel sensors configured to respond to electromagnetic radiation associated with different spectral channels. For example, the electromagnetic radiation sensor can include or be coupled to a Bayer filter with a filter pattern that includes 50% green-color-channel pixel sensors, 25% red-color-channel pixel sensors, and 25% blue-color-channel pixel sensors.

Referring back to FIG. 3B, if the pixel sensor includes or is coupled to a filter (e.g., a Bayer filter) that has groups of pixel sensors configured to variously respond to electromagnetic radiation associated with different spectral channels, a new signal (not shown) calculated based on signal 306 of the pixel sensor can be associated with a pixel location value after a demosaic calculation has been performed. For example, the new signal can be a signal calculated based on a demosaic algorithm and can be associated with a pixel location value defined based on the demosaic algorithm. In some embodiments, the pixel location value can be defined based on and/or can be associated with a location associated with an image or a location associated with a display.

A collection of narrow-band signal values (e.g., a collection of values based on signals such as signal 306 shown in FIG. 3B) can be used to produce a narrow-band image. Because signal 306 is a response from an emission from the narrow-band electromagnetic radiation source (shown in FIG. 3A), a full-color image cannot be produced without defining additional signal information (e.g., green signal information and/or blue signal information when red signal information is collected) based on, for example, a mathematical relationship.

Figure 3C:
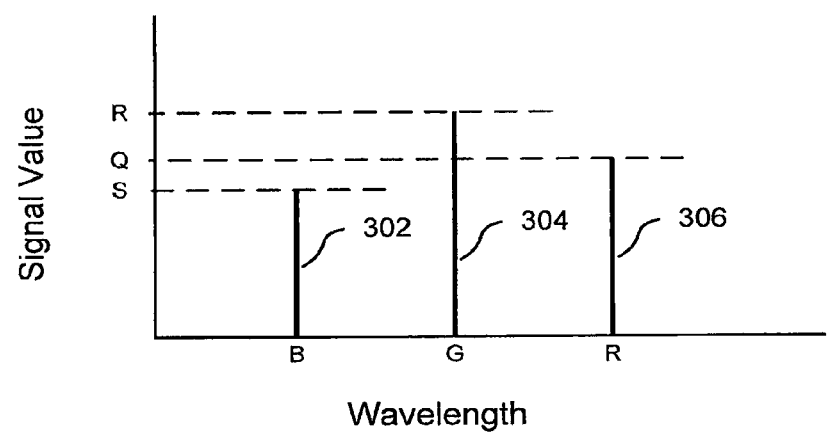
FIG. 3C is a schematic graph that illustrates a set of signal values calculated based on the response of the pixel sensor shown in FIG. 3B, according to an embodiment of the invention.

FIG. 3C is a schematic graph that illustrates a set of signal values calculated based on the response of the pixel sensor shown in FIG. 3B, according to an embodiment of the invention. The set of signals is associated with a spectral region of electromagnetic radiation include spectral region outside of spectral region 310 shown in FIG. 3A. Specifically, the response of the red-color-channel pixel sensor from FIG. 3B is used to define a set of signal values that includes a signal value associated with a red color channel, a signal value associated with a green color channel, and a signal value associated with a blue color channel. The wavelengths B and G shown in FIG. 3B correspond, respectively, with a wavelength of a blue color and a wavelength of a green color.

Signal 302 with a signal value of S at wavelength B, and signal 304 with a signal value of R at wavelength G are calculated based on the signal value of Q associated with signal 306 (also shown in FIG. 3B) at wavelength R. Signal 302 and signal 304 are, respectively, associated with wavelengths G and B, which fall outside of the spectral region 310 associated with the narrow-band electromagnetic radiation source (shown in FIG. 3A).

In this embodiment, because the signal values 302, 304, and 306 are each associated with a color from a full-color space, the signals 302, 304, and 306 can be used to produce a pixel associated with a full-color image. In some embodiments, signals 302 and 304 can each be associated with a spectral channel that overlaps with at least a portion of the spectral region 310 associated with the narrow-band electromagnetic radiation source (shown in FIG. 3A).

The signals 302 and 304 can be calculated based on a mathematical relationship defined based on a correlation between narrow-band responsiveness data associated with wavelength R and wide-band responsiveness data associated with the set of full-color wavelengths R, G, and B. Specifically, one or more portions of the mathematical relationship can be defined based on the narrow-band responsiveness data and the wide-band responsiveness data. Defining the mathematical relationship can include, for example, defining the form of the mathematical relationship, defining parameters/variables within the mathematical relationship, and/or coefficients within the mathematical relationship. After the mathematical relationship has been defined, the mathematical relationship can be used at one or more signal processing modules of an imaging system such as that shown in FIG. 1. More details related to a method for defining a mathematical relationship are described in connection with FIG. 6.

For example, a set of signal values (such as that described in connection with FIG. 3C) for a full-color pixel included in a wide-band vector $\overline{WB_{mn}}$ and associated with a pixel location value specified by row m and column n can be calculated using the mathematical relationship $\overline{WB_{mn}} = \overline{NB_{mn}} \cdot T$, which is expressed in general terms and where $\overline{NB_{mn}}$ can be a narrow-band vector. In this mathematical relationship $\overline{NB_{mn}} = (NB_{mn}^R)$, $\overline{WB_{mn}} = (WB_{mn}^R, WB_{mn}^G, WB_{mn}^B)$, and T is a 3×3 linear matrix of coefficients $$T = \begin{matrix} t_r^R & t_r^G & t_r^B \\ t_g^R & t_g^G & t_g^B \\ t_b^R & t_b^G & t_b^B \end{matrix}.$$

The signal value $NB_{mn}^R$ is also associated with pixel location value (m, n) and is defined in response to electromagnetic radiation emitted from a narrow-band electromagnetic radiation source associated with a red color channel (similar to that shown in FIG. 3A). The signal values $WB_{mn}^R$, $WB_{mn}^G$, $WB_{mn}^B$ are associated with the red color channel, a green color channel, and a blue color channel, respectively. A signal value for an individual color channel, such as the red color channel $WB_{mn}^R$, can thus be calculated as $WB_{mn}^R = NB_{mn}^R \cdot t_r^R$, which is an equation derived from the mathematical relationship $\overline{WB_{mn}} = \overline{NB_{mn}} \cdot T$. The red color channel $WB_{mn}^R$ is calculated based on the signal value $NB_{mn}^R$ and coefficient $t_r^R$ from matrix T. A signal value for the green color channel $WB_{mn}^G$ can be calculated in a like manner based on $NB_{mn}^R$.

The coefficients within matrix T can be defined so that when $\overline{NB_{mn}}$ is defined based on electromagnetic radiation reflected from an object after being emitted from a narrow-band electromagnetic radiation source, a set of signal values included in vector $\overline{WB_{mn}}$ can be calculated. If T is the identity matrix, $\overline{WB_{mn}}$ will be equal to $\overline{NB_{mn}}$.

In some embodiments, the matrix T (e.g., one or more of the coefficients of the matrix T) can be defined using a Finlayson Maximum Ignorance with Positivity (MIP) method. Details related to the Finlayson MIP method are described in Finlayson et al., "The Maximum Ignorance Assumption with Positivity," Final Program and Proceedings of the IS&T/SID Fourth Color Imaging Conference, pp. 202-205 (1996), which is incorporated herein by reference in its entirety. In some embodiments, the coefficients within matrix T can be defined by, for example, minimizing the least-squares error between any combination of variables and values included in narrow-band responsiveness data and wide-band responsiveness data. An example of wide-band responsiveness data and narrow-band responsiveness data is shown in FIG. 5.

In some embodiments, the mathematical relationship can be modified for any number of spectral channels. For example, the vector $\overline{NB_{mn}}$ can be defined to include signal values associated with two color channels within a narrow spectrum of electromagnetic radiation and the vector $\overline{WB_{mn}}$ can be defined to include signal values associated with three color channels over a spectral region of electromagnetic radiation broader than the narrow spectrum. In some embodiments, the matrix T can be referred to as a back projection transform matrix.

Figure 5:
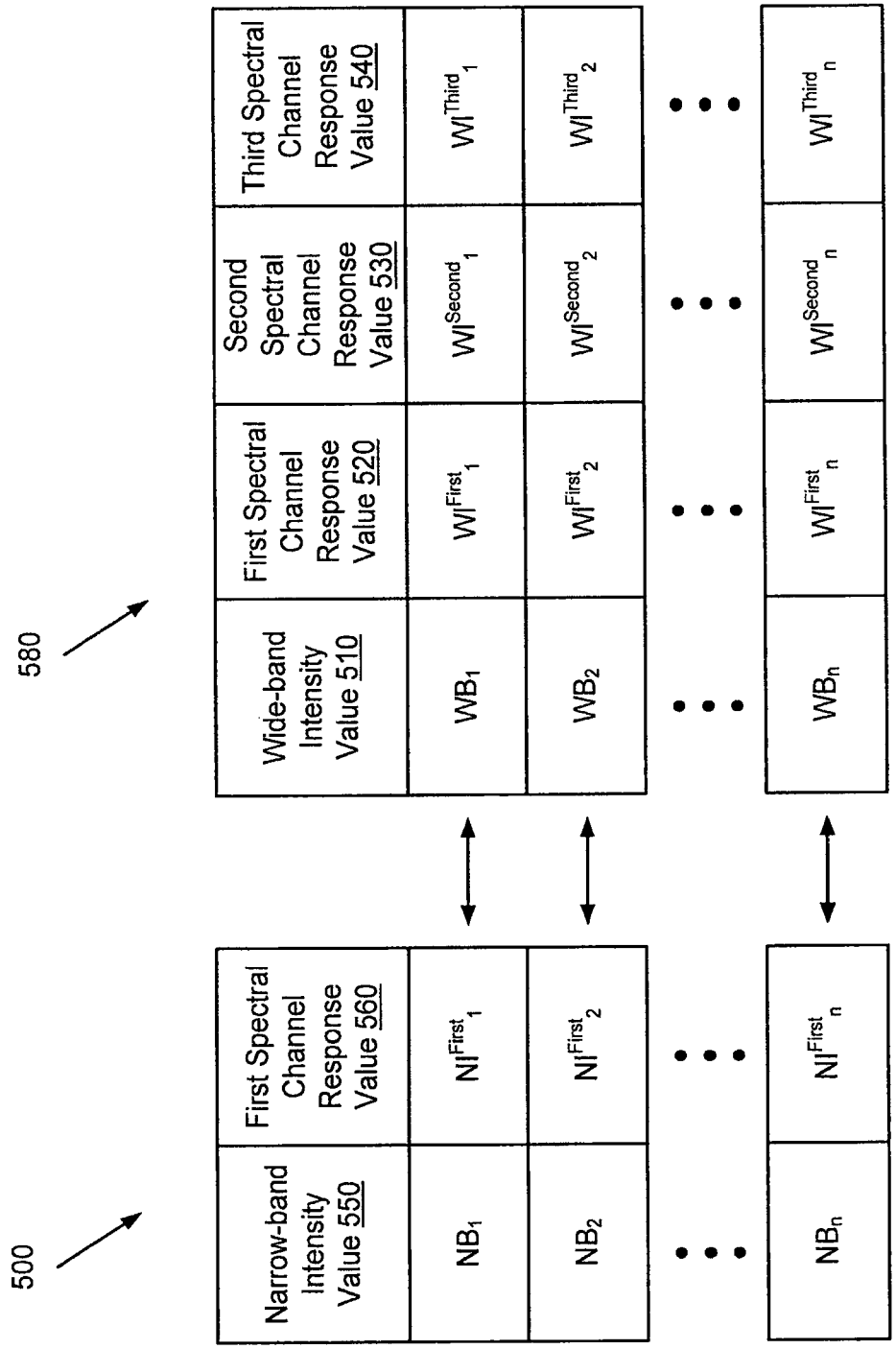
FIG. 5 illustrates narrow-band responsiveness data and wide-band responsiveness data that can be used to define a correlation, according to an embodiment of the invention.

FIG. 5 illustrates narrow-band responsiveness data 500 and wide-band responsiveness data 580 that can be used to define a correlation, according to an embodiment of the invention. The narrow-band responsive data 500 includes a set of first spectral channel response values 560 defined in response to electromagnetic radiation reflected from a target after being emitted from a narrow-band electromagnetic radiation source. For example, at narrow-band intensity value $NB_1$ (column 550), the first spectral channel response value is $NI^{First}_1$ (column 560).

The wide-band responsive data 580 includes a first spectral channel response value 520, a second spectral channel response value 530, and a third spectral channel response value 540. Each of the spectral channel response values 520, 530, and 540 are response values defined in response to electromagnetic radiation reflected from the target after being emitted from a wide-band electromagnetic radiation source at wide-band intensity values 510. For example, at wide-band intensity value $WB_1$ (column 510), the first spectral channel response value is $WI^{First}_1$ (column 520).

In some embodiments, the narrow-band responsiveness data 500 and the wide-band responsiveness data 580 can be produced by illuminating one or more targets (e.g., one or more images) from a target database using the narrow-band electromagnetic radiation source and the wide-band electromagnetic radiation source, respectively. In some embodiments, the narrow-band responsiveness data 500 and the wide-band responsiveness data 580 can be produced using archetypical electromagnetic radiation sources. For example, the narrow-band responsiveness data 500 and the wide-band responsiveness data 580 can be produced using an electromagnetic radiation source that is similar to those that would be used in an actual application. In some embodiments, the narrow-band responsiveness data 500 and the wide-band responsiveness data 580 can be produced under a variety of specified conditions (e.g., a specified temperature).

In some embodiments, the narrow-band responsiveness data 500 and the wide-band responsiveness data 580 can be used to produce a correlation expressed as a look-up table. In some embodiments, the narrow-band responsiveness data 500 and the wide-band responsiveness data 580 can be associated with a particular region of a sensor. Narrow-band responsiveness data 500 and/or wide-band responsiveness data 580 associated with the particular region can be referred to as region-specific data. Accordingly, a correlation produced based on the region-specific data can be used to calculate wide-band image data associated with the particular region of the sensor based on narrow-band image data associated at the particular region of the sensor.

Figure 6:
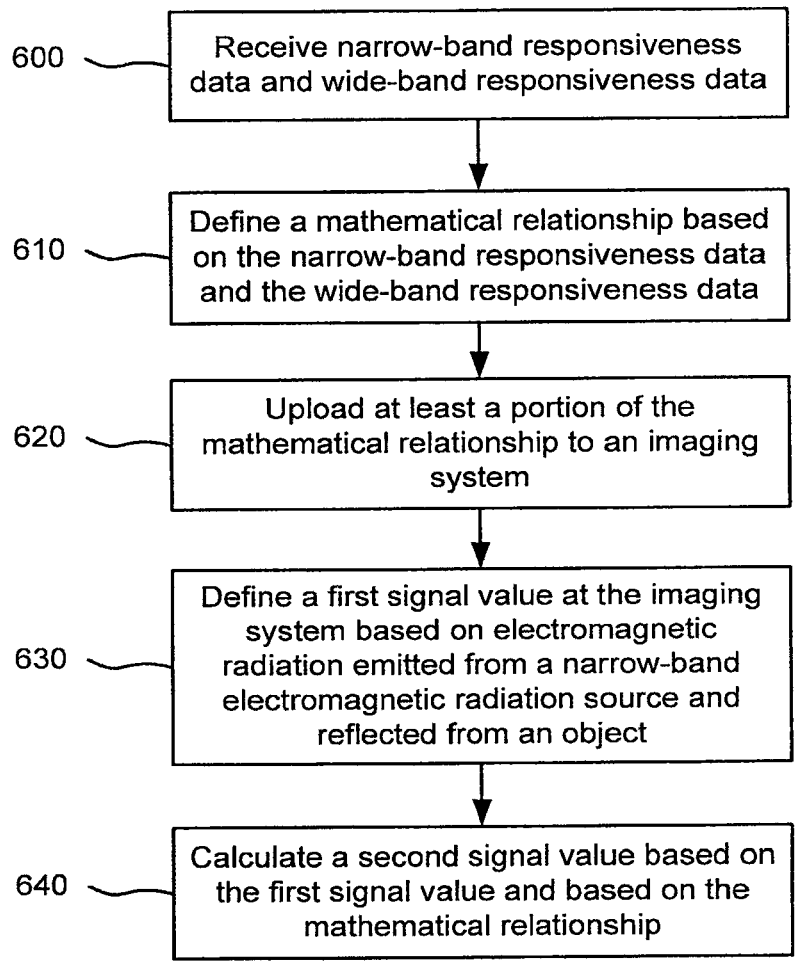
FIG. 6 is a flowchart that illustrates a calibration method, according to an embodiment of the invention.

FIG. 6 is a flowchart that illustrates a calibration method, according to an embodiment of the invention. As shown in the flowchart, narrow-band responsiveness data and wide-band responsiveness data are received at 600. In some embodiments, the narrow-band responsiveness data and the wide-band responsiveness data can be similar to that shown in FIG. 5.

A mathematical relationship (also can be referred to as a calibrated relationship) is defined based on the narrow-band responsiveness data and the wide-band responsiveness data at 610. Defining the mathematical relationship can include, for example, defining the form of the mathematical relationship, defining parameters/variables within the mathematical relationship, and/or coefficients within the mathematical relationship.

At least a portion of the mathematical relationship is uploaded to an imaging system at 620. In some embodiments, the mathematical relationship and/or portions of the mathematical relationship (e.g., only coefficients) can be uploaded to one or more imaging systems. In some embodiments, the mathematical relationship can be defined within a set of instructions (e.g., a computer program, a computer application) uploaded to an imaging system. In some embodiments, a library of mathematical relationships, parameters/variables, and/or coefficients associated with one or more narrow-band electromagnetic radiation sources and/or wide-band electromagnetic radiation sources can be uploaded to an imaging system.

A first signal value is defined at the imaging system based on electromagnetic radiation emitted from a narrow-band electromagnetic radiation source and reflected from an object at 630. In some embodiments, the first signal value can be, for example, an intensity value.

A second signal value is calculated based on the first signal value and based on the mathematical relationship at 640. The second signal value can be associated with a wide-band electromagnetic radiation spectrum (e.g., an electromagnetic radiation spectrum associated with a wide-band light source). In some embodiments, the mathematical relationship can be selected from a library of mathematical relationships based on the narrow-band electromagnetic radiation source.

Figure 7:
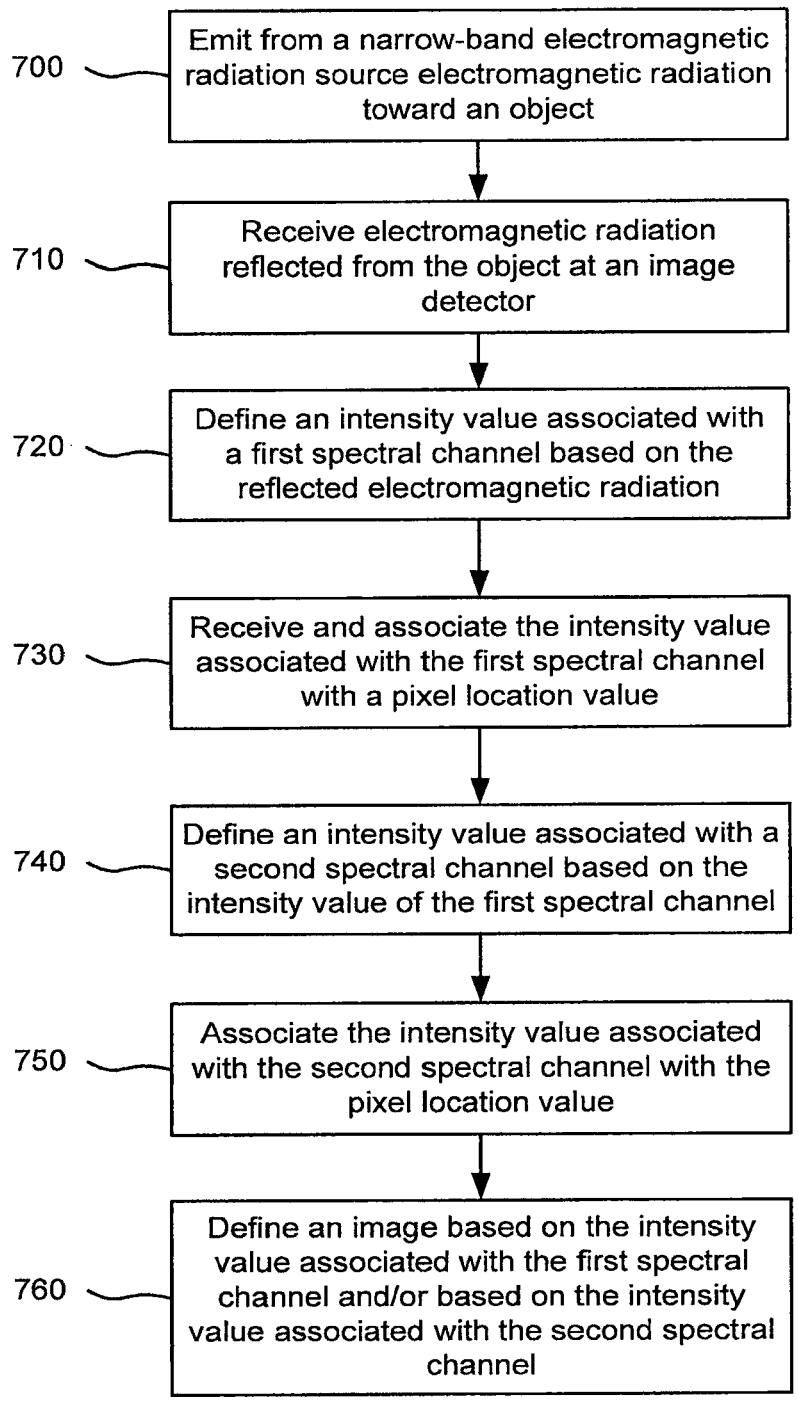
FIG. 7 is a flowchart that illustrates a method for calculating an intensity value associated with a spectral channel based on an intensity value associated with a different spectral channel, according to an embodiment of the invention.

FIG. 7 is a flowchart that illustrates a method for calculating an intensity value associated with a spectral channel based on an intensity value associated with a different spectral channel, according to an embodiment of the invention. As shown in the flowchart, electromagnetic radiation is emitted from a narrow-band electromagnetic radiation source toward an object at 700. The electromagnetic radiation can be substantially centered around a particular wavelength of electromagnetic radiation associated with a specified visible color. In some embodiments, the narrow-band electromagnetic radiation source can emit a region of electromagnetic radiation that is associated with a spectral channel (e.g., red color channel).

Electromagnetic radiation reflected from the object is received at an image detector at 710. The image detector can include, for example, one or more lenses, processing elements, and/or a sensor such as a CCD sensor or sensor with a Bayer filter.

An intensity value associated with a first spectral channel is defined based on the reflected electromagnetic radiation at 720. The intensity value can be defined based on, for example, a voltage signal from the image detector. The first spectral channel can be associated with a region of electromagnetic radiation that substantially corresponds with a region of electromagnetic radiation associated with the narrow-band electromagnetic radiation source.

The intensity value associated with the first spectral channel is received and associated with a pixel location value at 730. The pixel location value can be associated with a pixel sensor from a CCD sensor, a location (e.g., a pixel) associated with an image, and/or a location (e.g., a pixel) associated with a display. In some embodiments, the intensity value can be associated with the pixel location value (block 730) simultaneous to the intensity value being defined (block 720).

An intensity value associated with a second spectral channel is defined based on the intensity value of the first spectral channel at 740 and a correlation between narrow-band responsiveness data and wide-band responsiveness data. The narrow-band responsiveness data can be associated with a responsiveness of a sensor to a electromagnetic radiation from a narrow-band electromagnetic source (e.g., a red LED). The wide-band responsiveness data can be associated with a responsiveness of a sensor to a electromagnetic radiation from a wide-band electromagnetic source (e.g., a white light source).

The second spectral channel can be associated with a region of electromagnetic radiation different than a region of electromagnetic radiation associated with the narrow-band electromagnetic radiation source and/or the first spectral channel. In some embodiments, the first spectral channel and the second spectral channel can be associated with regions of electromagnetic radiation that at least partially overlap. The second spectral channel can be associated with a region of electromagnetic radiation that is within a region of electromagnetic radiation emitted by the wide-band electromagnetic radiation source.

An intensity value of the second spectral channel is associated with the pixel location value at 750. The intensity value of the first spectral channel and the intensity value of the second spectral channel can be associated with the pixel location value within a database.

An image is defined based on the intensity value associated with the first spectral channel and/or based on the intensity value associated with the second spectral channel at 760. In some embodiments, the intensity value associated with the first spectral channel and the intensity value associated with the second spectral channel can be used to define a pixel within an image. For example, if the first spectral channel is a green color channel and the second spectral channel is a red color channel, the intensity value associated with the first spectral channel and the intensity value associated with the second spectral channel can be used to produce a pixel that has a color that is a mixture of green and red. In some embodiments, any combination of the intensity values can be used to produce multiple images simultaneously (e.g., multiple images displayed on multiple displays) or separately (e.g., multiple images displayed on a single display).

In some embodiments, if the intensity value associated with the first spectral channel and the intensity value associated with the second spectral channel are associated with a first color space (e.g., an RGB color space), the intensity values can be combined and/or translated into a different color space (e.g., a hue-saturation-brightness (HSB) color space, a hue-saturation-lightness (HSL) color space). Although this embodiment is related to the calculation of intensity values, the flowchart can be applied to the calculation of any type of image data (e.g., a raw signal value from a sensor).

FIGS. 8A through 8E are schematic graphs that illustrate intensity values calculated based on responses from two different narrow-band electromagnetic emissions at different times, according to an embodiment of the invention. The x-axis of all of the graphs is wavelength, and the y-axis of all of the graphs is intensity value.

Figure 8A:
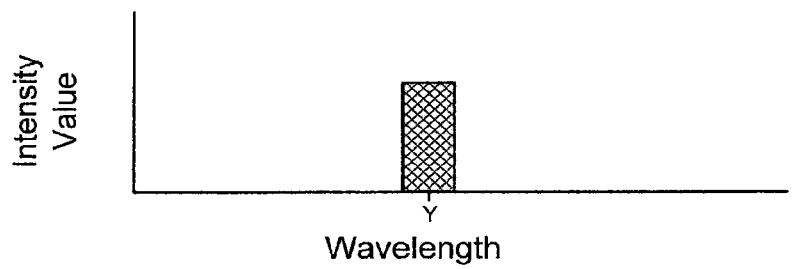
FIG. 8A is a schematic graph that illustrates an electromagnetic radiation emission from a first narrow-band electromagnetic radiation source, according to an embodiment of the invention.

FIG. 8A is a schematic graph that illustrates an electromagnetic radiation emission from a first narrow-band electromagnetic radiation source, according to an embodiment of the invention. As shown in FIG. 8A, the electromagnetic radiation emission is substantially centered around a wavelength Y.

Figure 8B:
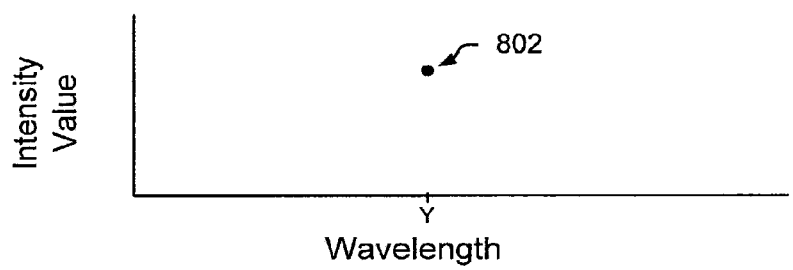
FIG. 8B is a schematic graph that illustrates a response of a pixel sensor to the electromagnetic radiation emission shown in FIG. 8A, according to an embodiment of the invention.

FIG. 8B is a schematic graph that illustrates a response of a pixel sensor to the electromagnetic radiation emission shown in FIG. 8A, according to an embodiment of the invention. In this embodiment, the response is shown as a point 802 that has an intensity value at wavelength Y. In some embodiments, the pixel sensor can be configured to only produce a signal in response to electromagnetic radiation emitted at wavelength Y.

Figure 8C:
FIG. 8C is a schematic graph that illustrates an electromagnetic radiation emission from a second narrow-band electromagnetic radiation source that occurs after the electromagnetic radiation emission shown in FIG. 8A, according to an embodiment of the invention.

FIG. 8C is a schematic graph that illustrates an electromagnetic radiation emission from a second narrow-band electromagnetic radiation source that occurs after the electromagnetic radiation emission shown in FIG. 8A, according to an embodiment of the invention. As shown in FIG. 8C, the electromagnetic radiation emissions is substantially centered around a wavelength Z.

Figure 8D:
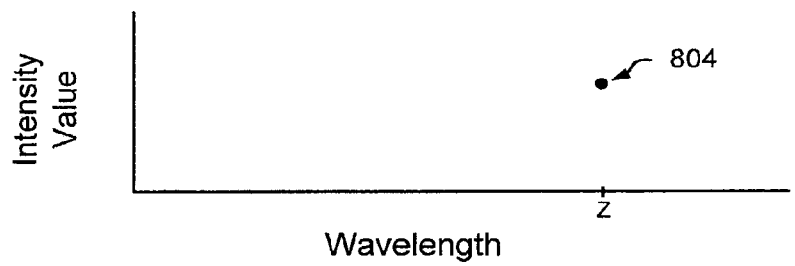
FIG. 8D is a schematic graph that illustrates a response of a pixel sensor to the electromagnetic radiation emission shown in FIG. 8C, according to an embodiment of the invention.

FIG. 8D is a schematic graph that illustrates a response of a pixel sensor to the electromagnetic radiation emission shown in FIG. 8C, according to an embodiment of the invention. In this embodiment, the response is shown as a point 804 that has an intensity value at wavelength Z. In some embodiments, the pixel sensor can be configured to produce a signal only in response to electromagnetic radiation emitted at wavelength Z. Even though the responses shown in FIGS. 8B and 8D, respectively, can be defined based on signals from different pixel sensors, the responses can be associated with a single pixel location value.

Figure 8E:
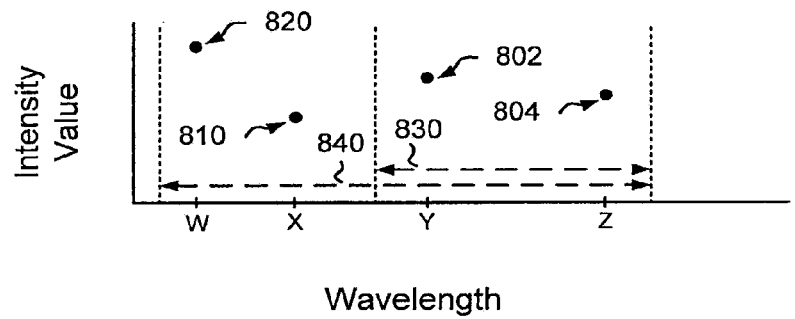
FIG. 8E is a schematic graph that illustrates intensity values calculated based on the pixel responses shown in FIGS. 8B and 8D, according to an embodiment of the invention.

FIG. 8E is a schematic graph that illustrates intensity values calculated based on the pixel responses shown in FIGS. 8B and 8D, according to an embodiment of the invention. Specifically, point 810 at wavelength X and point 820 at wavelength W are calculated based on the intensity values associated with points 802 and 804. The points 810 and 820 can be associated with the same pixel location value with which points 820 and 804 are associated. The intensity values associated with points 802, 804, 810, and 820 can be used to calculate a pixel value that can be used to produce an image that has a portion corresponding to the pixel location value. In some embodiments, any combination of the intensity values associated with points 802, 804, 810, and 820 can be used to produce multiple images simultaneously or in succession.

The wavelengths Y and Z fall within a narrow-band spectral region 830 and the wavelengths W, X, Y, and Z fall within a wide-band spectral region 840. Moreover, the wavelengths W and X fall outside of the narrow-band spectral region 830. The points 810 and 820 are calculated based on a correlation between narrowband responsiveness data and wide-band responsiveness data. In some embodiments, the narrow-band responsiveness data can be based on data associated with wavelengths included in the narrow-band spectral region 830 and the wide-band responsiveness data based on data associated with wavelengths included in the wide-band spectral region 840.

Some embodiments of the invention relate to a computer storage product with a computer-readable medium (also can be referred to as a processor-readable medium) having instructions or computer code thereon for performing various computer-implemented operations. The media and computer code (also referred to as code) may be those specially designed and constructed for the specific purpose or purposes. Examples of computer-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks; carrier wave signals; and hardware devices that are specially configured to store and execute program code, such as Application Specific Integrated Circuits ("ASICs"), Programmable Logic Devices ("PLDs"), and Read-Only Memory ("ROM") and Random-Access Memory ("RAM") devices. Examples of computer code include, but are not limited to, micro-code or microinstructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. An imaging method, comprising:
   receiving an intensity value of a first spectral channel associated with a pixel location, wherein the intensity value of the first spectral channel is based on electromagnetic radiation reflected from an object after being emitted from a narrow-band electromagnetic radiation source;
   defining an intensity value of a second spectral channel based on the intensity value of the first spectral channel, wherein the second spectral channel is associated with a spectral region of electromagnetic radiation different from a spectral region of electromagnetic radiation associated with the first spectral channel, and wherein the spectral region of the second spectral channel is different from a spectral region of the narrow-band electromagnetic radiation source; and
   associating the intensity value of the second spectral channel with the pixel location.

2. The imaging method of claim 1, further comprising calculating the intensity value of the first spectral channel based on a demosaic algorithm.

3. The imaging method of claim 1, wherein the spectral region of electromagnetic radiation associated with the first spectral channel is separate from the spectral region of electromagnetic radiation associated with the second spectral channel.

4. The imaging method of claim 1, wherein the pixel location is associated with a pixel, and wherein a spectral region of electromagnetic radiation associated with the pixel is modified in response to associating the intensity value of the second spectral channel with the pixel location.

5. The imaging method of claim 1, further comprising receiving an intensity value of a third spectral channel associated with the pixel location, wherein the third spectral channel is associated with a spectral region of electromagnetic radiation different from the spectral region of electromagnetic radiation associated with the second spectral channel, and wherein defining the intensity value of the second spectral channel is based on the intensity value of the third spectral channel.

6. The imaging method of claim 1, wherein defining the intensity value of the second spectral channel is based on a linear mathematical relationship.

7. The imaging method of claim 1, wherein defining the intensity value of the second spectral channel is based on a coefficient associated with the first spectral channel and a coefficient associated with the second spectral channel.

8. The imaging method of claim 1, further comprising defining a first pixel of a first image based on the intensity value of the first spectral channel and the intensity value of the second spectral channel, wherein the first pixel is associated with the pixel location.

9. The imaging method of claim 8, further including defining a second pixel of a second image based on the intensity value of the first spectral channel and not based on the intensity value of the second spectral channel, wherein the second pixel is associated with the pixel location.

10. The imaging method of claim 1, further comprising: receiving a plurality of signals based on the electromagnetic radiation reflected from the object after being emitted from the narrow-band electromagnetic radiation source, the intensity value of the first spectral channel being associated with the plurality of signals, wherein at least a portion of an image of the object is based on the plurality of signals, the portion of the image being associated with the spectral region associated with the second spectral channel.

11. The imaging method of claim 1, wherein the spectral region associated with the second spectral channel includes at least a portion of the spectral region associated with the first spectral channel.

12. The imaging method of claim 10, wherein the image is a red-green-blue (RGB) image, the spectral region associated with the first spectral channel is a narrow-band spectral region, and the spectral region associated with the second spectral channel is a red-green-blue (RGB) spectral region.

13. The imaging method of claim 10, wherein the electromagnetic radiation is reflected at a first time, and the plurality of signals is a first plurality of signals, and wherein the method further comprises receiving a second plurality of signals based on electromagnetic radiation reflected at a second time from the object after being emitted from a second electromagnetic radiation source having a third spectral region of electromagnetic radiation, wherein the third spectral region of electromagnetic radiation is different than the spectral region associated with the first spectral channel.

14. The imaging method of claim 13, further including defining the at least a portion of the image of the object based on the second plurality of signals.

15. The imaging method of claim 13, wherein the spectral region associated with the second spectral channel includes at least a portion of the spectral region associated with the first spectral channel and at least a portion of the third spectral region.

16. The imaging method of claim 10, further including defining the at least a portion of the image of the object based on a back projection transform matrix.

17. The imaging method of claim 1, wherein the spectral region of the second spectral channel is broader than the spectral region of the first spectral channel.

18. The method of claim 1, wherein the pixel location is associated with a pixel sensor forming part of an electromagnetic sensor.

19. An imaging method, comprising:
   receiving an intensity value of a first spectral channel associated with a pixel location, wherein the intensity value of the first spectral channel is based on electromagnetic radiation reflected from an object after being emitted from a narrow-band electromagnetic radiation source;
   defining an intensity value of a second spectral channel based on the intensity value of the first spectral channel, wherein the second spectral channel is associated with a spectral region of electromagnetic radiation different from a spectral region of electromagnetic radiation associated with the first spectral channel, and wherein at least a portion of the spectral region associated with the second spectral channel is outside of a spectral region of the narrow-band electromagnetic radiation source; and
   associating the intensity value of the second spectral channel with the pixel location.

20. An imaging method, comprising:
   receiving an intensity value of a first spectral channel associated with a pixel location, wherein the intensity value of the first spectral channel is based on electromagnetic radiation reflected from an object after being emitted from a narrow-band electromagnetic radiation source;
   defining an intensity value of a second spectral channel based on the intensity value of the first spectral channel, wherein the second spectral channel is associated with a spectral region of electromagnetic radiation different from a spectral region of electromagnetic radiation associated with the first spectral channel, and wherein the second spectral channel is outside of a spectral region of the narrow-band electromagnetic radiation source; and
   associating the intensity value of the second spectral channel with the pixel location.

* * * * *